United States Patent [19]
Vaughn et al.

[11] Patent Number: 5,284,134
[45] Date of Patent: Feb. 8, 1994

[54] SWIVEL CONNECTOR

[76] Inventors: E. Lanny Vaughn, 4334 Heights Ave.; James Cromwell, 2225-A Freed Way, both of Pittsburg, Calif. 94565

[21] Appl. No.: 913,828

[22] Filed: Jul. 16, 1992

Related U.S. Application Data

[63] Continuation-in-part of Ser. No. 849,272, Mar. 11, 1992, Pat. No. 5,222,486.

[51] Int. Cl.$^5$ ............................................. A61M 39/00
[52] U.S. Cl. .................... 128/200.24; 128/DIG. 26; 128/912; 604/283; 604/905; 285/98
[58] Field of Search .............. 604/283, 905, 408, 243; 128/207.19, 207.18, 204.18, 911, 912, DIG. 26, 202.27, 200.24; 285/98, 275, 276, 281

[56] References Cited

U.S. PATENT DOCUMENTS

| | | | |
|---|---|---|---|
| 2,764,430 | 9/1956 | Roberts | 285/245 |
| 2,876,535 | 3/1959 | Ray | 285/98 X |
| 3,972,321 | 8/1976 | Proctor | 128/DIG. 26 X |
| 4,152,017 | 5/1979 | Abramson | 128/207.14 X |
| 4,187,846 | 2/1980 | Lolachi | 604/905 X |
| 4,588,402 | 5/1986 | Igari | 604/408 |
| 4,687,235 | 8/1987 | Stoll | 285/98 X |
| 4,723,948 | 2/1988 | Clark | 604/905 X |
| 4,747,621 | 5/1988 | Gans | 285/275 X |
| 4,915,104 | 4/1990 | Marcy | 128/207.18 |
| 5,062,420 | 11/1991 | Levine | 128/204.18 |
| 5,092,854 | 3/1992 | Black | 604/243 |
| 5,222,486 | 6/1993 | Vaughn | 128/200.24 |

FOREIGN PATENT DOCUMENTS

| | | | |
|---|---|---|---|
| 3536924 | 7/1986 | Fed. Rep. of Germany | 285/98 |
| 2399608 | 4/1979 | France | 285/275 |

Primary Examiner—Edgar S. Burr
Assistant Examiner—Eric P. Raciti

[57] ABSTRACT

A swivel connector is provided for use in either an intravenous liquid supply line or an oxygen supply line to allow the line to rotate to prevent kinking. A body portion is provided having a cylindrical cavity formed in one end thereof, and a hollow, cylindrical male member slides into the cylindrical cavity and has sufficient clearance to allow free rotation of the male member within the cylindrical cavity. A locking flange is carried by the male member which engages an annular groove formed in the body portion to prevent the male member from inadvertently disengaging from the body portion. A seal is also provided between the male member and the body.

1 Claim, 2 Drawing Sheets

SWIVEL CONNECTOR

CROSS-REFERENCE TO RELATED APPLICATION

This application is a continuation-in-part of U.S. application Ser. No. 07/849,272 filed Mar. 11, 1992, now U.S. Pat. No. 5,222,486 issued Jun. 29, 1993.

BACKGROUND

This invention relates generally to a swivel connector for use in either an intravenous liquid supply line or an oxygen supply line to allow the line to rotate and to prevent kinking of the line.

The prior art includes U.S. Pat. No. 4,875,718 dated Oct. 24, 1989 to Marken, which teaches a ball and socket swivel connector for oxygen lines. However, the ball and socket joint of Marken relies on a fairly close fit between the ball and socket to prevent leakage of oxygen. The tighter the fit between the ball and socket, the more difficult it is for the mechanism to swivel. Furthermore, both ends of the ball and socket connector may rotate if the friction between the ball and socket is sufficiently great. The present invention provides a swivel connector in which oxygen leakage is held to a minimum but wherein the swivel is allowed to rotate freely, because a relatively small surface area is involved in the sealing mechanism of the present invention. Furthermore, the present invention provides a clip attached to the user's clothing which prevents rotation of the body portion of the connector.

The prior art also includes U.S. Pat. No. 4,915,104 dated Apr. 10, 1990 to Marcy. This patent teaches a nasal oxygen tube support which includes a clip used to help support a part of the oxygen tubing. However, this patent does not teach a swivel connector.

The prior art also includes U.S. Pat. No. 5,054,482 dated Oct. 8, 1991 to Bales. This patent teaches a rotatable tracheostomy tube which does include a rotatable connector. However, this connector is extremely cumbersome in design, particularly as applied in an oxygen line.

The prior art also includes U.S. Pat. No. 4,588,402 dated May 13, 1986 to Igari et al. This patent teaches a quick connector for medical fluid lines which is impervious to bacteria. The Igari device is primarily a quick connecting device rather than a freely rotating swivel mechanism.

BRIEF SUMMARY OF THE INVENTION

The present invention provides a very simple but extremely effective swivel connector for intravenous liquid supply lines or oxygen supply lines. The mechanism utilizes two parts, a male and female part, together with a locking mechanism and a sealing mechanism. The male member is slid into the female member, the locking mechanism becomes engaged and the male member is permanently held in place. The male member rotates freely to allow the line to rotate and to prevent kinking of the line. An optional clip may be utilized with the design to prevent rotation of the upper half of the swivel mechanism relative to the body of the user.

Accordingly, a primary object of the invention is to provide a small but effective swivel connector for use in intravenous liquid supply lines and oxygen supply lines which freely rotates with the slightest rotational pressure applied.

Another object of the invention is to provide a locking swivel connector for use in intravenous liquid and oxygen supply lines which incorporates a foolproof locking mechanism which allows the connector to freely rotate without coming apart and thereby interrupting the flow of life sustaining fluids.

Another object of the invention is to provide a swivel connector for intravenous liquid and oxygen supply lines having a clip attachable to the user's clothing which prevents the upper portion of the connector from rotating relative to the user's body.

Other objects and advantages of the invention will become apparent from the following description of the preferred embodiment and the drawings wherein:

DETAILED DESCRIPTION OF THE DRAWINGS

Figure 1:
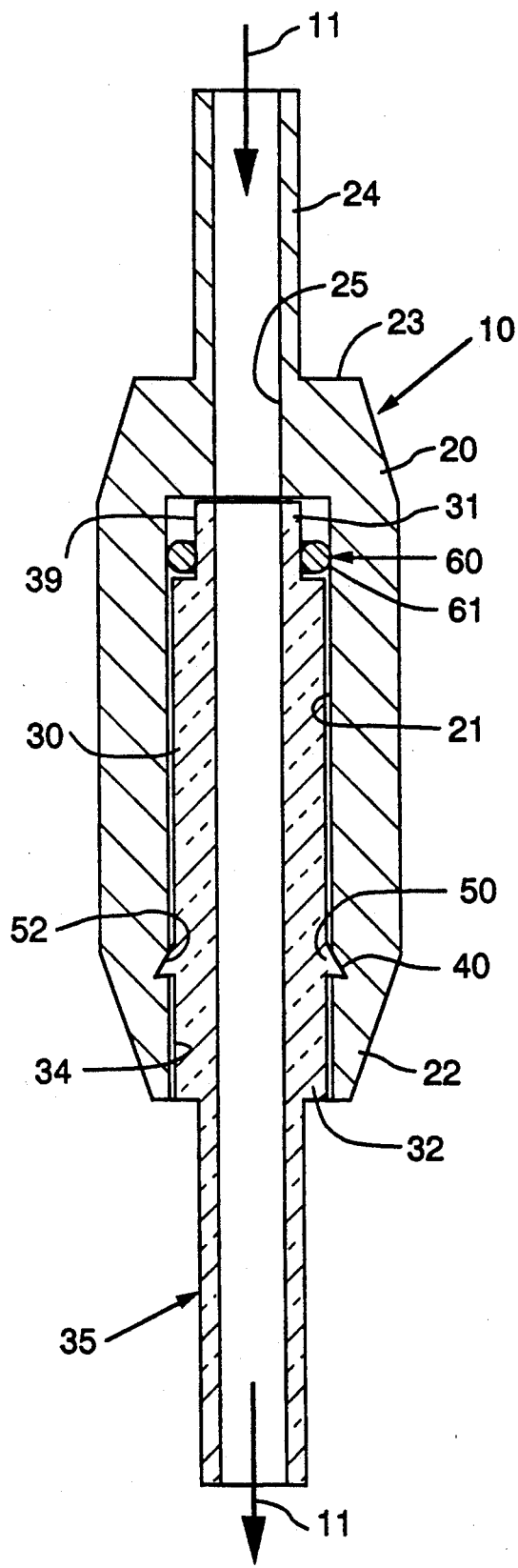
FIG. 1 is a sectional view of the swivel connector of the present invention.

As shown in FIG. 1, swivel connector shown generally as 10 is provided for use in either an intravenous liquid supply line or an oxygen supply line through which fluid flows along the path indicated by arrow 11.

The connector includes a body portion 20 having a first lower end 22 in which cylindrical cavity 21 is formed. The body 20 also has a second upper end 23 having a passageway 25 which communicates with cylindrical cavity 21. The axial length of cylindrical cavity 21 in the preferred embodiment is at least three times as great as the diameter of cavity 21. Body portion 20 may be made of flexible and resilient plastic. The upper portion of body 20 connects to a hollow, cylindrical inlet 24 which may be connected to an intravenous liquid supply line or an oxygen supply line by conventional fittings.

A hollow cylindrical male member 30 is provided which is adapted to slide into and to rotate within cylindrical cavity 21. Male member 30 is a hollow cylindrical tube having a distal end 31 and a proximal end 32. The axial length of male member 30 is the same as the axial length of cylindrical cavity 21. The axial length of male member 30 in the preferred embodiment is at least three times as great as the diameter of member 30. We have found that the use of a relatively elongated male member in conjunction with a relatively elongated cylindrical cavity provides stability to the swiveling action of the connector. The outer diameter of male member 30 is less than the diameter of cylindrical cavity to provide clearance between the two, which clearance allows for free rotation of member 30 within cavity 21. Male member 30 may be made of a flexible and resilient plastic similar to that used in body portion 20.

A groove 40 is provided in body portion 20. Groove 40 extends circumferentially around and opens into cylindrical cavity 21. Groove 40 as a cross-section which is generally V-shaped and which forms an acute angle with cylindrical cavity 21.

A locking flange means or retaining means 50 is formed on the surface of said male member 30 near the proximal end 32. In the preferred embodiment, the locking flange means 50 comprises a circumferential flange 52 which extends continuously around the circumference of male member 30. The preferred embodiment of the flange also includes a flange of generally V-shaped cross-section which forms an acute angle with the surface 34 of male member 30. As shown in FIG. 1, locking flange means 50 engages groove 40 when the male member 30 is slid into cylindrical cavity 21. The locking action is caused by the acute angle of flange 52 engaging the acute angle of groove 40 which prevents removal of the male member 30 from the cylindrical cavity 21 without destroying the swivel. This locking mechanism provides a full-proof manner of assuring that the swivel connector will not come apart and thereby threaten the supply of life sustaining fluid to the user.

A sealing means 60 is also provided for sealing male member 30 relative to body portion 20. Sealing means 60 in the preferred embodiment comprises an O-ring 61 which is carried by the distal end 31 of male member 30. The distal end 31 has a reduced diameter section 39 which carries O-ring 61.

It is understood that alternate sealing means may be provided between the male member 30 and cylindrical cavity 21. It is also to be understood that various forms of locking or retaining means may be utilized. For example, the locking means 50 may comprise a flange which is not continuous around the entire 360° periphery of male member 30. Similarly, the groove may be carried by the male member 30 as opposed to the body portion 20 and variations in design of the groove may also be utilized.

In operation, the swivel connector 10 is inserted into an intravenous liquid supply line or an oxygen supply line with inlet 24 in the upward position as shown in FIG. 1. A supply line or adapter is slipped over inlet 24. At the bottom portion of swivel connector 10 an outlet 35 is provided which connects to the lower or proximal end 32 of male member 30. The outlet 35 is connected to an intravenous liquid supply line or oxygen supply line which goes to the user. As the user moves about, the outlet 35 may rotate freely with male member 30 relative to body portion 20. By being able to freely rotate, the line which is attached to outlet 35 does not become kinked and threaten the supply of fluids to the user.

Figure 2:
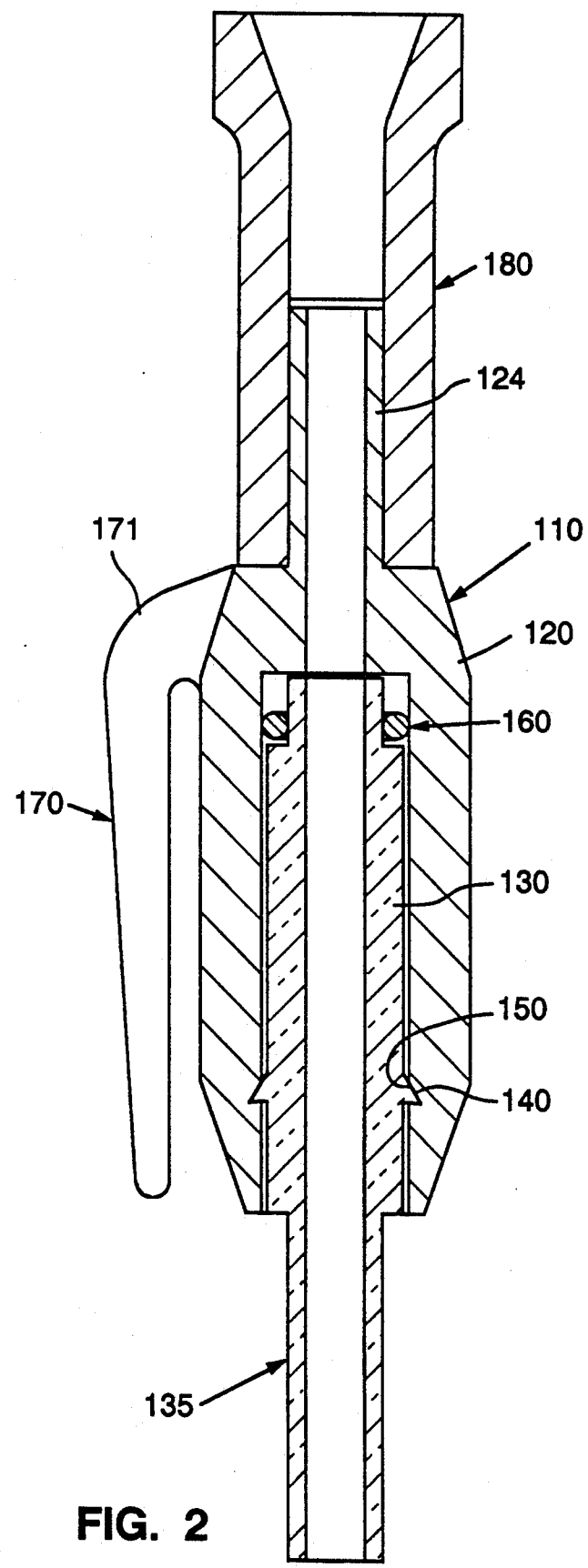
FIG. 2 is a sectional view of an alternate embodiment of the swivel connector of the present invention.

FIG. 2 shows an alternate embodiment 110 which utilizes an identical body portion 120, male member 130, groove 140, locking means 150 and sealing means 160 and which also utilizes an optional clip means 170 comprising an arm 171 carried by body portion 120 which may be attached to clothing of the user. This prevents the body portion 120 of the swivel connector 110 rotating relative to the body of the user. Also shown in FIG. 2 is an adapter 180 that may be connected to inlet 124. Adapter 180 is then connected to an intravenous liquid supply line or an oxygen supply line.

We claim:

1. A two-piece, locking swivel connector for use in either an intravenous liquid supply line or an oxygen supply line, comprising:

a body portion having a cylindrical cavity formed in one end thereof, the length of said cylindrical cavity being at least three times as great as its diameter, a hollow, cylindrical male member having distal and proximal ends, said member being adapted to slide into and to rotate within said cylindrical cavity, the length of said male member being at least three times as great as its diameter, a groove formed in said body, said groove extending circumferentially around and opening into said cylindrical cavity, said groove having a cross-section which forms an acute angle with said cylindrical cavity, locking flange means formed on the surface of and near the proximal end of said male member, said locking flange means forming an acute angle with the surface of said male member, whereby said locking flange means engages said groove when said male member is slid into said cylindrical cavity, the acute angle of said locking flange means engaging the acute angle of said groove, preventing removal of said male member from said cylindrical cavity, said male member having a reduced diameter projecting portion at its distal end, and sealing means comprising an O-ring carried by said projecting portion, the distance between said O-ring and said locking flange means of said male member being greater than the diameter of said male member.

* * * * *